(12) United States Patent
Cromwell et al.

(10) Patent No.: US 7,170,605 B2
(45) Date of Patent: Jan. 30, 2007

(54) ACTIVE SENSOR AND METHOD FOR OPTICAL ILLUMINATION AND DETECTION

(76) Inventors: Evan Francis Cromwell, 820 Vista Dr., Redwood City, CA (US) 94062; Andrei Brunfeld, 10178 Ridgeway Dr., Cupertino, CA (US) 95014

( * ) Notice: Subject to any disclaimer, the term of this patent is extended or adjusted under 35 U.S.C. 154(b) by 450 days.

(21) Appl. No.: 10/647,855

(22) Filed: Aug. 25, 2003

(65) Prior Publication Data
US 2005/0046847 A1 Mar. 3, 2005

(51) Int. Cl.
*G01N 21/25* (2006.01)
(52) U.S. Cl. ..................................... 356/417
(58) Field of Classification Search .................... None
See application file for complete search history.

(56) References Cited

U.S. PATENT DOCUMENTS

| | | | | |
|---|---|---|---|---|
| 5,674,698 | A * | 10/1997 | Zarling et al. | 422/52 |
| 6,043,880 | A * | 3/2000 | Andrews et al. | 422/52 |
| 6,606,553 | B2 * | 8/2003 | Zobell et al. | 701/120 |
| 6,825,927 | B2 * | 11/2004 | Goldman et al. | 356/317 |
| 2002/0008871 | A1 * | 1/2002 | Poustka et al. | 356/317 |

* cited by examiner

*Primary Examiner*—Gregory J. Toatley, Jr.
*Assistant Examiner*—Juan D. Valentin, II

(74) *Attorney, Agent, or Firm*—Jeffrey D. Moy; Harry M. Weiss; Weiss & Moy, P.C.

(57) ABSTRACT

An active sensor a method for optical illumination and detection provides low cost and high-speed optical scanning of bio-arrays, DNA samples/chips, semiconductors, micro-electromechanical systems and other samples requiring inspection or measurement. A plurality of illumination sources forming a parallel multi-pixel array is used to illuminate one or more samples via an imaging system or by placement in close proximity to the samples. The array may be a line array or a two-dimensional array. A plurality of detectors is integrated within the multi-pixel illumination array or provided in a separate array, each detector for detecting optical properties of the sample that results from illumination by one or more associated illumination sources. One detector may be associated with multiple illuminators or one illuminator may be associated with multiple detectors. Filters may be integrated within the illumination path and/or detection paths to provide wavelength and/or polarization discrimination capability and microlenses may also be incorporated within the illumination path and/or detection paths to provide focusing or imaging. The illumination sources may be provided by TFT-LCD devices, diode emitters, organic LEDs (OLEDs), vertical cavity emitting lasers (VCELs) or other light sources that may be integrated to form a high-density illumination matrix. The detectors may be PIN photo-diodes or other suitable detectors that are capable of integration within the illumination matrix.

33 Claims, 5 Drawing Sheets

ACTIVE SENSOR AND METHOD FOR OPTICAL ILLUMINATION AND DETECTION

BACKGROUND OF THE INVENTION

1. Field of the Invention

The present invention relates generally to optical measurement systems, and more specifically, to an active sensor illumination and detection apparatus for performing sample measurements using associated detector/illuminator groups integrated on one or more substrates.

2. Background of the Invention

One-dimensional and two dimensional measurement and inspection of samples is commonly performed in many industries, including biotechnology, semiconductor, micro electro-mechanical systems (MEMS) and others. For example, in the biotechnology industry, fluorescence measurements are used to determine the response of biological matter to illumination, thus revealing information about the composition and structure of a sample. Typically, for biological fluorescence tests, a sample or a material that is introduced to a sample is "tagged" with a fluorescent compound, the sample is illuminated with a laser, and the resulting fluorescent emissions are mapped to determine the locations of the fluorescent compound after interaction with the sample. For example, a prospective cancer drug may be tagged with a fluorescent compound and introduced to a sample having cancerous tissue. Then the sample is washed to remove excess fluorescent compound. The sample is illuminated and resulting fluorescent emissions are mapped to determine whether or not the prospective drug has bound to the cancer active sensor cells.

The above-described process is typically performed on a bio array, which may be a sample of DNA, gene chips including multiple DNA strands, microtiter plates with wells filled with various biocompounds, or microfluidic lab-on-a-chip devices. In each case, the device or sample is illuminated, typically by a scanning laser or filtered light source. Then, the resulting fluorescence (or lack thereof) is mapped. The mapping is typically performed by either a scanning confocal microscope (SCM) or by imaging onto a charge-coupled-device (CCD) sensor.

The disadvantages of the above-described systems and methods are long scanning times and moving parts for the SCM-based approach and lack of sensitivity and poorer spatial resolution for the CCD-based approach. A third alternative has been implemented, using a scanning laser and a photomultiplier tube for detection, but the cost of the scanning laser and detectors is a disadvantage, as well as the requirement of a moving mechanism.

In another application, in the inspection of color quality in materials, for example dye color, the sample may be illuminated and the sample's optical behavior measured to determine the properties of the sample. Measurement may be made of reflectivity, absorption, transmission, secondary emission or other optical property in order to determine sample characteristics. In order to measure a sufficient field of view, precise control over the color and angular spectrum must be maintained for both illumination and detection systems. The above requirements necessarily add tremendous complexity to any measurement tool.

In the field of MEMS and semiconductor manufacture, repetitive patterns are inspected for defects or anomalies. The device under inspection is illuminated and scattered and/or reflected light is imaged to determine properties of the device under inspection. Such illumination and detection techniques can be quite complex in order to provide the necessary sensitivity and resolution.

Therefore, it is desirable to provide an alternative method and system for providing active illumination and detection for one-dimensional and two-dimensional inspection of samples having low cost, sufficient resolution, high sensitivity and high scanning speed for a broad range of applications.

SUMMARY OF THE INVENTION

The above objectives of providing a method and system for performing active one-dimensional and two-dimensional optical measurements having high speed, high sensitivity and low cost is accomplished in a method and apparatus. The apparatus comprises an active sensor including multiple illumination sources integrated to form a multi-pixel matrix. The matrix may have multiple rows and columns or may include just one row.

Multiple detectors are also integrated within illumination source matrix, each for detecting optical behavior of a sample resulting from the illumination of the sample by one or more of the illumination sources. One detector may be associated with multiple illuminators or one illuminator may be associated with multiple detectors. Filters may be integrated within the illumination and/or detection paths for providing wavelength and/or polarization discrimination capability and lenses may also be integrated within the illumination and/or detection paths providing variable working distances. A lens may be shared between one or more detectors and one or more illumination sources.

The foregoing and other objectives, features, and advantages of the invention will be apparent from the following, more particular, description of the preferred embodiment of the invention, as illustrated in the accompanying drawings, wherein like reference designators indicate like elements.

DETAILED DESCRIPTION OF THE EMBODIMENTS

While the below description is limited, by the way of example, to the measurement of a fluorescent sample, it is understood that the function will be similar for samples such as colored materials, MEMS or semiconductor devices, and/or repetitive patterns, and other applications. In order to avoid repetition, it is understood that the same description will be applicable to other applications that measure optical properties of samples.

Figure 1:
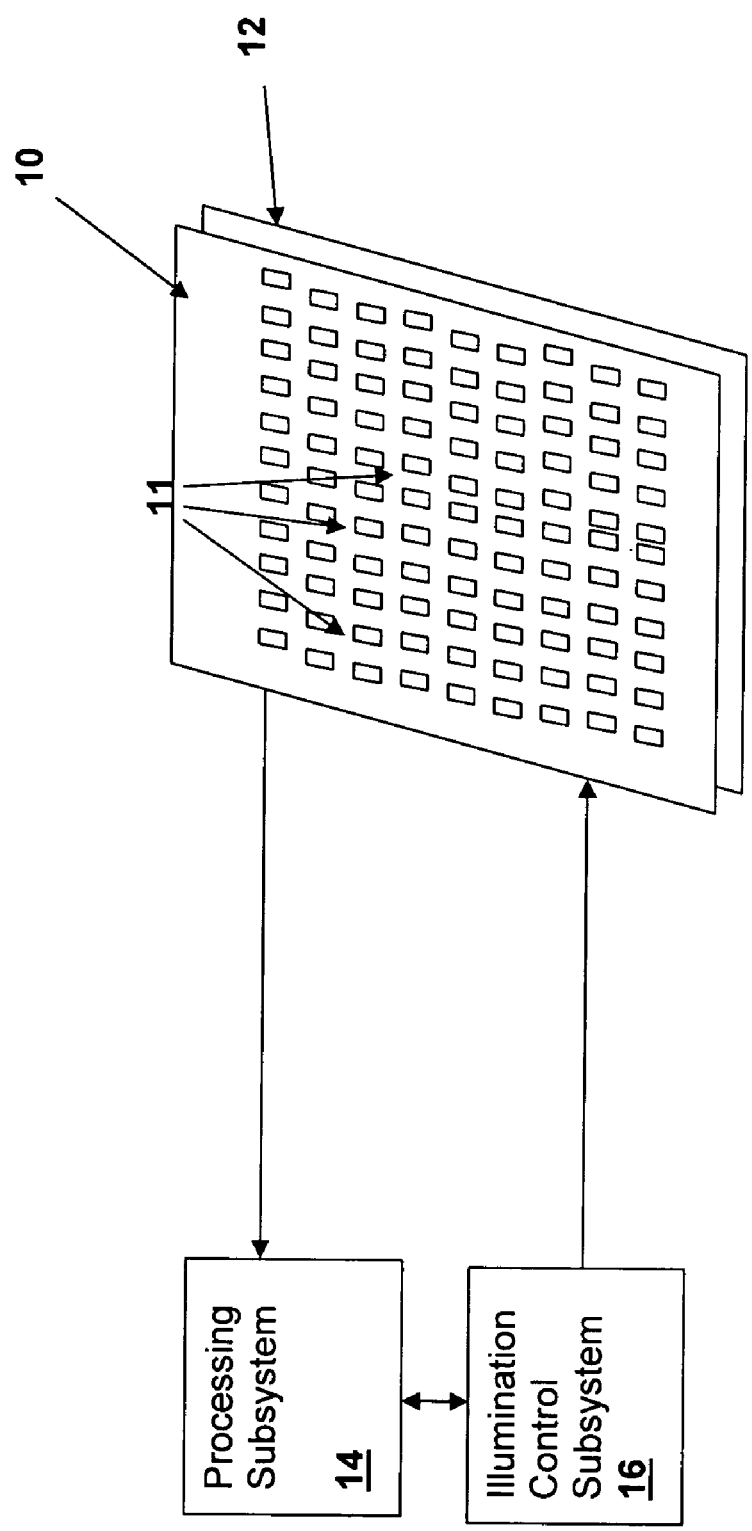
FIG. 1 is a pictorial diagram depicting an active sensor system including an apparatus in accordance with an embodiment of the present invention.

Referring now to the figures and in particular to FIG. 1, a system including an active sensor 10 in accordance with an embodiment of the present invention is shown. Active sensor 10, which includes a plurality of active sensor active sensor cells 11, is placed in close proximity with a sample frame 12, that may contain samples of biological matter tagged with a fluorescent material, or other samples under inspection such as a semiconductor device, for which a standard handling frame may be employed. Active sensor cells 11 each include one or more detectors and one or more illumination elements integrated on the substrate. While the depiction shows a two-dimensional active sensor 10, active sensor 10 may also be a one-dimensional active sensor, comprising only one row of active sensor cells 11.

The detection elements within active sensor cells 11 are coupled to a processing subsystem for detecting light scattered or emitted from associated portions of the samples. The association is by virtue of the proximity of the active sensor cells 11 to the sample frame 12 so that the fields of the detectors generally do not substantially overlap, or so that any overlap is generally limited to adjacent pixels. Similarly, the illumination element fields also do not substantially overlap in general and can be used to selectively illuminate portions of the samples. Sample frame 12 may comprise a plurality of wells, as in a microtiter plate or other multi-sample/multi-cell device, in which case, the spacing and location of active sensor cells 11 can be dictated by the spacing and location of wells in sample frame 12. One cell 11 may correspond to a single well, giving active sensor 10 the ability to simultaneously process optical information at each cell without requiring a scanning mechanism.

Alternatively, sample frame 12 may comprise a single contiguous sample, such as a tissue sample or single sample having multiple discrete portions such as a DNA gel. Where discrete boundaries are not present, it may be desirable to sequentially illuminate the illumination elements individually, or program an illumination pattern such that adjacent illumination elements do not cause illumination of portions of a sample associated with other illumination elements. Illumination control subsystem 16 provides for control of illumination elements within active sensor cells 11 and is coupled to a processing subsystem 14 that receives the outputs of detectors within active sensor cells 11. The interconnection of illumination control subsystem 16 with processing subsystem 14 permits synchronization of illumination and detection permitting accurate determination of response time and correlation of detected fluorescent emissions to the activation of an illumination element within a cell 11. In addition, illumination elements can be pulsed or modulated and detection elements can be shuttered or time-gated to allow complex temporally resolved measurement schemes.

In other embodiments of the present invention, sample frame 12 may hold samples comprising a matrix of colored elements or samples may have a scattering pattern such as found on MEMS or semiconductor devices. The function of the system is identical to that described previously except that the detected light is no longer fluorescent emission, but scattered light.

The illumination elements included within active sensor cells 11 are substrate-integrated sources that may be provided by TFT-LCD devices, diode emitters, organic LEDs (OLEDs), vertical cavity emitting lasers (VCELs) or other light sources that may be integrated to form a high-density illumination matrix. The detectors included within active sensor cells 11 may be PIN photo-diodes, CCD sensors, CMOS sensors or other detectors that are suitable for integration within the illumination matrix. Lenses are optionally included for coupling a cell or field of active sensor cells 11 to samples or portions thereof and may be implemented using standard microlenses, graded-refractive-index (GRIN) lenses, fiber couplers or other suitable focusing/coupling or imaging mechanism.

Figure 2A:
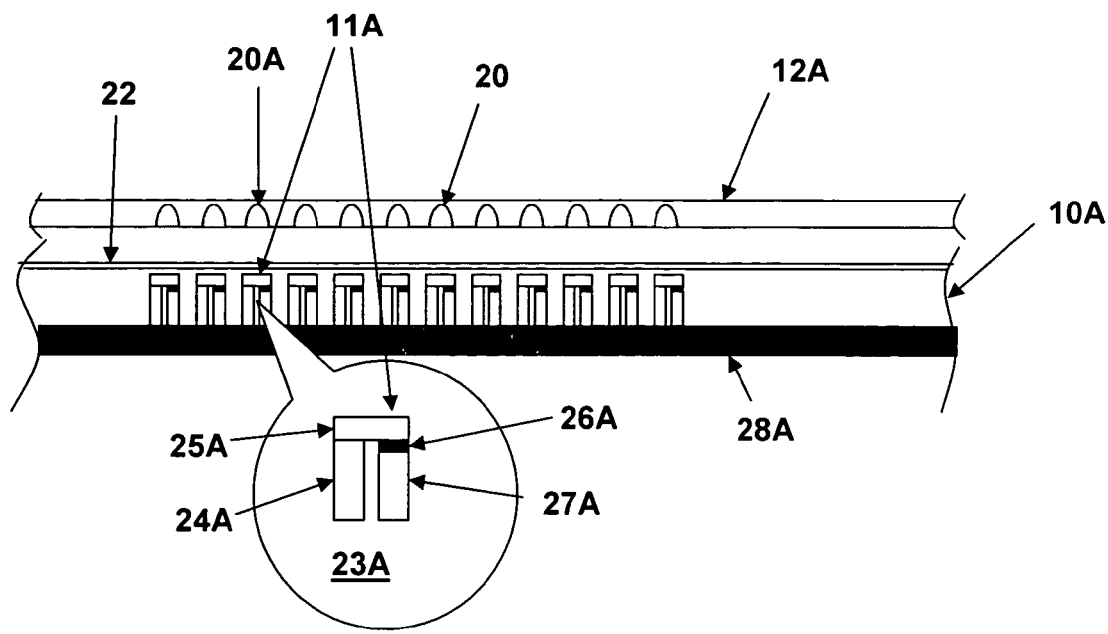
FIG. 2A is a pictorial diagram depicting details of an active sensor in accordance with an embodiment of the present invention.

Referring now to FIG. 2A, details of an active sensor 10A including active sensor cells 11A, in accordance with an embodiment of the present invention are shown. FIG. 2A also shows an exemplary sample frame 12A including sample elements 20 (depicted as wells in a microtiter plate) that are associated with particular active sensor cells 11A via proximity of sample frame 12A to active sensor 10A. A substrate 28A supports active sensor cells 11A and a cover glass 22 is optionally included to protect active sensor cells 11A and may be spaced above active sensor cells 11A as shown, or placed in contact with active sensor cells 11A.

The structure of active sensor cells 11A is shown in balloon 23A. A single illumination element 24A is paired (associated) with a single detector 27A for detecting fluorescence of biological matter deposited in an associated sample element 20A due to illumination from illumination element 24A (or other optical characteristics in non-fluorescence measurements). A microlens 25A is optionally integrated over illumination element 24A and detector 27A for focusing or imaging a field of illumination element 24A and detector 27A on or within sample element 20A. A filter 26A is integrated between detector 27A and microlens 25A for providing a passband response around a specific optical wavelength and/or a polarization characteristic, providing wavelength and/or polarization selectivity in the output response of detector 27A, whereby a specific fluorescence band is detected by detector 27A. Illumination element 24A is generally a narrowband emitter in the present configuration, but in some applications may be a broadband source, depending on whether or not the measurement being made is dependent on a specific excitation wavelength. The embodiment depicted in FIG. 2A, is exemplary of a single-detector, single-illumination element pairing that is associated with a unique portion of a sample or unique samples of a sample frame by virtue of the sample proximity. Other configurations depicted in other embodiments below or otherwise understood to be encompassed by the present invention include other groupings of multiple or single detectors to multiple or single illumination elements or arrangements including a multi-pixel illumination element array interspersed with a multi-pixel detector array where no specific grouping of detectors and illumination elements is employed. Similarly, it is understood that various geometric arrangements of the illumination/detector pair can be used, including side-by-side, concentric arrangements, quad detectors and others and that an imaging system may be used so that the array or arrays do not have to be placed in close proximity to the samples.

Figure 2B:
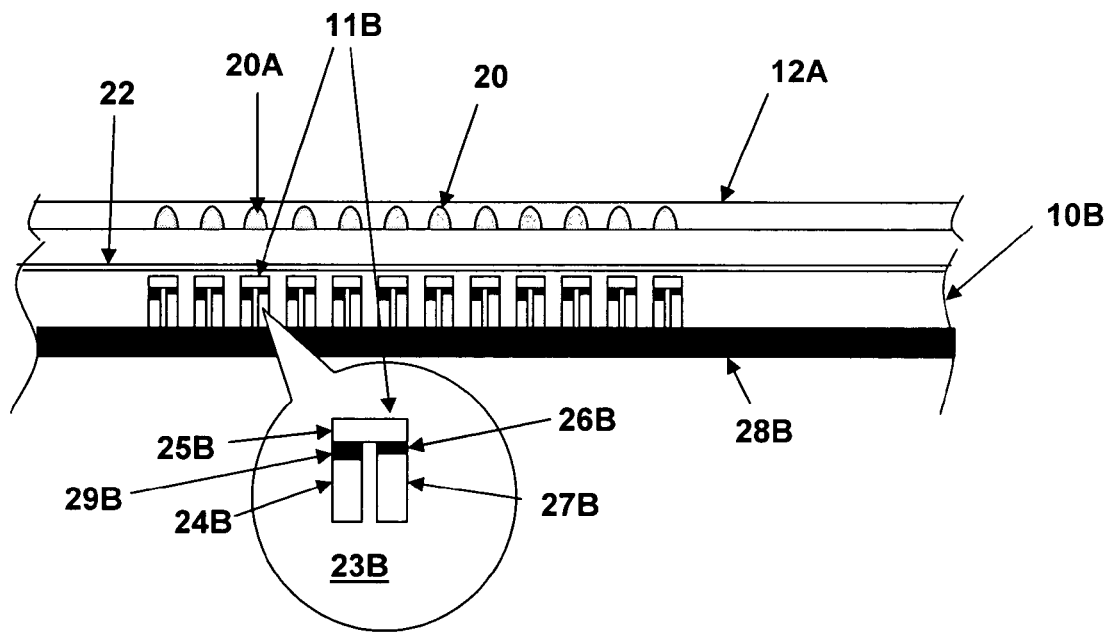
FIG. 2B is a pictorial diagram depicting details of an active sensor in accordance with another embodiment of the present invention.

Referring now to FIG. 2B, details of an active sensor 10B including active sensor cells 11B, in accordance with another embodiment of the present invention are shown. FIG. 2B also shows an exemplary sample frame 12A including sample elements 20 that are associated with particular active sensor cells 11B via proximity of sample frame 12A to active sensor 10B. A substrate 28B supports active sensor cells 11B and cover glass 22 is optionally included to protect active sensor cells 11B and may be spaced above active sensor cells 11B as shown, or placed in contact with active sensor cells 11B.

The structure of active sensor cells 11B is shown in balloon 23B. A single illumination element 24B is paired (associated) with a single detector 27B for detecting fluorescence of biological matter deposited in an associated cell forming sample element 20A due to illumination from illumination element 24B (or measuring other optical characteristics in non-fluorescence measurements). A microlens 25B is optionally integrated over illumination over illumination element 24B and detector 27B for focusing or imaging a field of illumination element 24B and detector 27B on or within well 20A. A filter 29B is integrated between illumination element 24B and microlens 25B for providing a passband response around a specific optical wavelength and/or polarization characteristic, providing a narrowband and/or polarization-controlled illumination source. Illumination element 24B is generally a broadband emitter in the present configuration.

Another filter 26B is integrated between detector 27B and microlens 25B for providing a passband response around a specific optical wavelength and/or a polarization characteristic, providing wavelength and/or polarization selectivity in the output response of detector 27B, whereby a specific fluorescence band is detected by detector 27B. Filters 26B and 29B are not constrained to have the same passband wavelength, as the fluorescent response of a material may differ greatly from the specific excitation wavelength used to excite the biological sample. The embodiment of cell 11B depicted in FIG. 2B is another example of a single-detector single-illumination element pairing. Other possible combinations include a filtered illumination source with an unfiltered detector, polarized illumination source with filtered detector and other combinations of passband and/or polarizer filters.

Figure 2C:
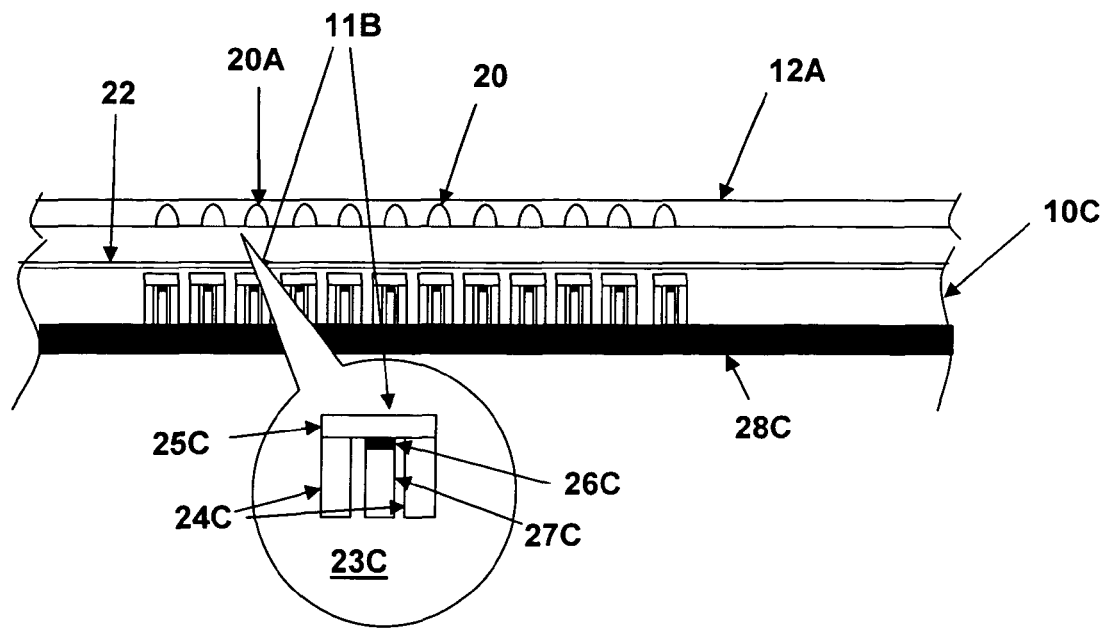
FIG. 2C is a pictorial diagram depicting details of an active sensor in accordance with yet another embodiment of the present invention.

Referring now to FIG. 2C, details of an active sensor 10C including active sensor cells 11C, in accordance with yet another embodiment of the present invention are shown. FIG. 2C also shows an exemplary sample frame 12A including sample elements (wells) 20 that are associated with particular active sensor cells 11C via proximity of sample frame 12A to active sensor 10C. A substrate 28C supports active sensor cells 11C and cover glass 22 is optionally included to protect active sensor cells 11C and may be spaced above active sensor cells 11C as shown, or placed in contact with active sensor cells 11C.

The structure of active sensor cells 11C is shown in balloon 23C. Multiple illumination elements 24C are paired (associated) with a single detector 27C for detecting fluorescence of biological matter deposited in an associated sample element 20A due to illumination from illumination elements 24C (or other optical characteristics in non-fluorescence measurements). A microlens 25C is optionally integrated over illumination over illumination elements 24C and detector 27C for focusing or imaging a field of illumination elements 24C and detector 27C on or within well 20A. A filter 26C is integrated between detector 27C and microlens 25C for providing passband response around a specific optical wavelength and/or a polarization characteristic, providing wavelength and/or polarization selectivity in the output response. Illumination elements 24C are generally narrowband emitters having separate predetermined illumination wavelengths in the present configuration and are generally controlled by illumination control subsystem 16 so that fluorescent response of samples or portions thereof to multiple predetermined wavelength excitation can be determined by enabling first one set of illumination elements in active sensor cells 11C corresponding to a first wavelength and then a second set of illumination elements in active sensor cells 11C corresponding to a second wavelength and observing the response using detectors 27C. The embodiment depicted in FIG. 2C is an example of multiple-illumination element, single-detector grouping. The number of associated illumination elements to a single detector also may be greater than two.

Figure 2D:
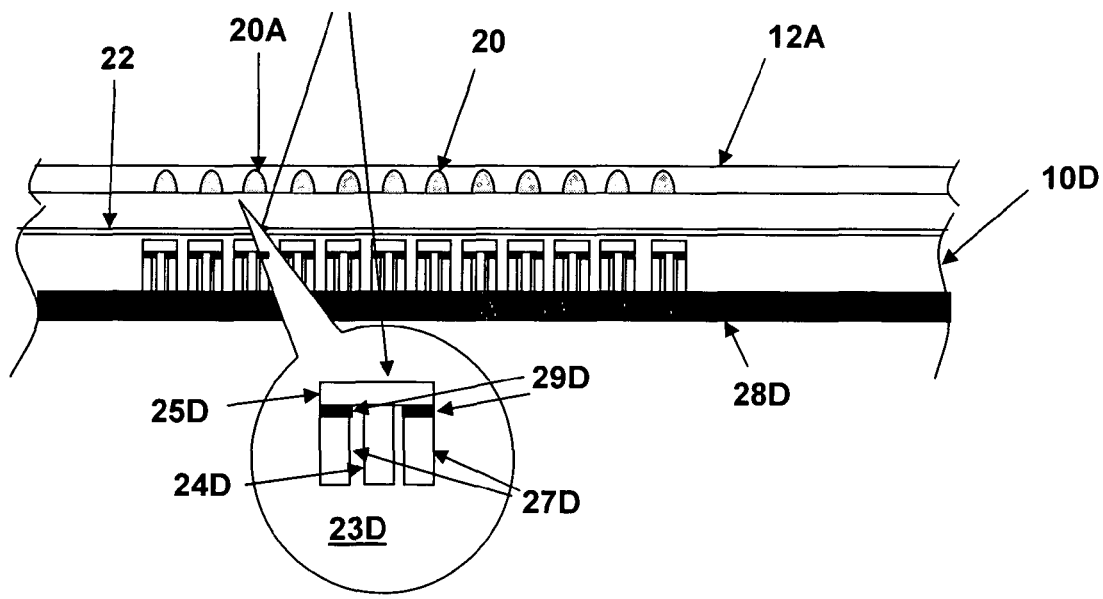
FIG. 2D is a pictorial diagram depicting details of an active sensor in accordance with still another embodiment of the present invention.

Referring now to FIG. 2D, details of an active sensor 10D including active sensor cells 11D, in accordance with still another embodiment of the present invention are shown. FIG. 2D also shows an exemplary sample frame 12A including sample elements (wells) 20 that are associated with particular active sensor cells 11D via proximity of sample frame 12A to active sensor 10D. A substrate 28D supports active sensor cells 11D and cover glass 22 is optionally included to protect active sensor cells 11D and may be spaced above active sensor cells 11D as shown, or placed in contact with active sensor cells 11D.

The structure of active sensor cells 11D is shown in balloon 23D. Multiple detectors 27D are paired (associated) with a single illumination element 24D for detecting fluorescence of biological matter deposited in an associated sample element 20A due to illumination from illumination element 24D (or other optical characteristics in non-fluorescence measurements). A microlens 25D is optionally integrated over illumination element 24D and detectors 27D for focusing or imaging a field of illumination element 24D and detectors 27D on or within well 20A. Multiple filters 29D are integrated between detectors 27D and microlens 25D for providing a unique passband response around a specific optical wavelength for each detector 27D in a cell 11D, providing multiple narrowband detector responses. Alternatively or in combination, filters 29D may provide multiple polarization responses, providing the ability to determine polarization ratios, and so forth. Illumination element 24D is generally a narrowband emitter for exciting a sample or portions thereof and detectors 27D in conjunction with filters 29D provide separate responses to the illumination, whereby multiple fluorescence band emissions can be simultaneously detected in response to narrowband excitation. The embodiment depicted in FIG. 2D is an example of single-illumination element, multiple-detector grouping. The number of associated detectors to a single illumination element also may be greater than two.

Figure 3:
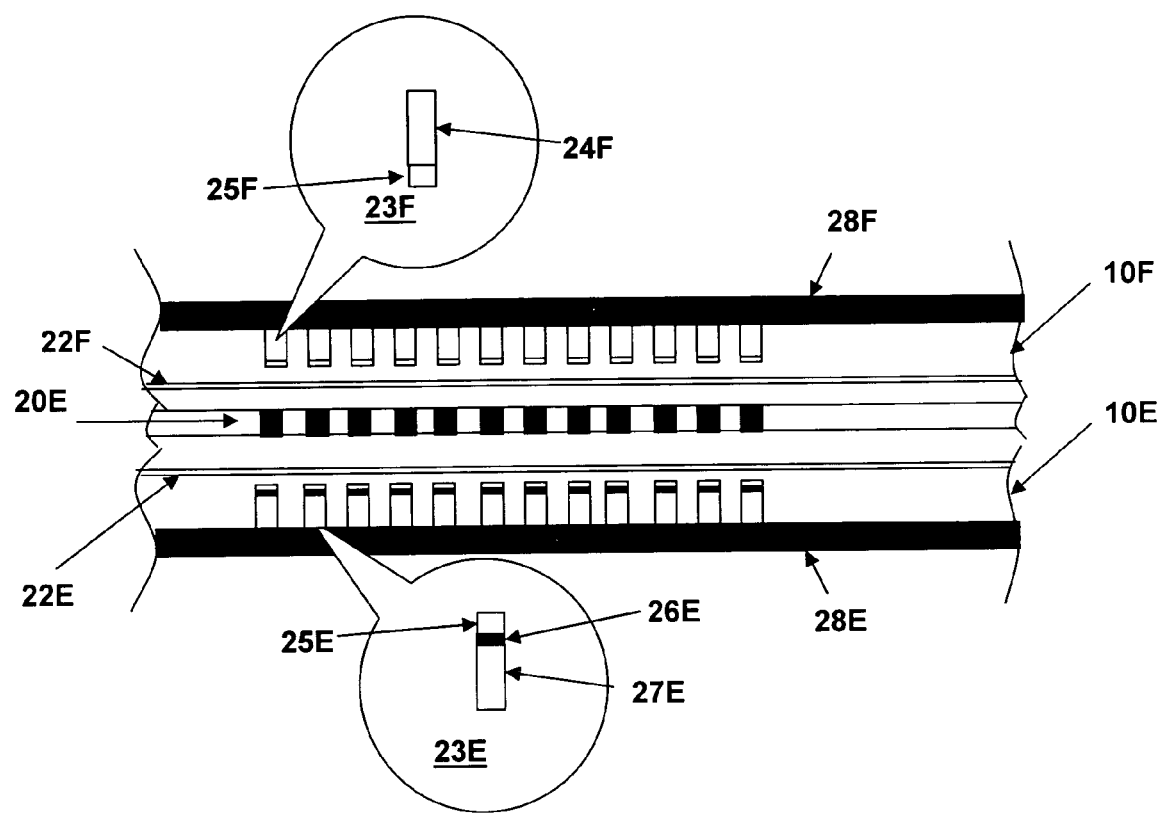
FIG. 3 is a pictorial diagram depicting details of an active sensor in accordance another embodiment of the present invention.

Referring now to FIG. 3, details of an active sensor system in accordance with an embodiment of the present invention are shown. Two separate array devices are employed, device 10E is a detection array that includes elements as depicted in balloon 23E, including detectors 27E filters 26E and microlens 25E. Device 10F is an illumination array including illumination elements 24F and microlenses 25F as depicted in balloon 23F. However, the elements may be variations on the depicted structure in accordance with the above-described element types and either or both arrays may include both illumination and detection elements. For example to provide a transmission and reflection/scattering measurement, device 10F may also include detection elements for detecting back-scattered light associated with each illumination element and/or sample element 20E.

The system of FIG. 3 is particularly suited for transmission measurements as detector device 10E is on the opposite side of samples 20E from illumination device 10F. Groups associating detectors 27E and illumination elements 24F in the system of FIG. 3 are associated by the location the fields of light transmitted by particular illumination elements 24F and received by particular detectors 27E, rather than also being associated by proximity as in the other exemplary embodiments described above, and as such, comprise the active sensor "cells" in the present embodiment. Both device 10E and device 10F are fabricated on substrates (28E and 28F respectively) and may include cover glasses (22E and 22F respectively). It should be noted in all of the above examples, filtering may be provided by a "gel" or colored cover glass that is provided in addition to or in place of the illustrated cover glasses for providing a wavelength/or polarization filtered optical characteristic within the system.

Figure 4:
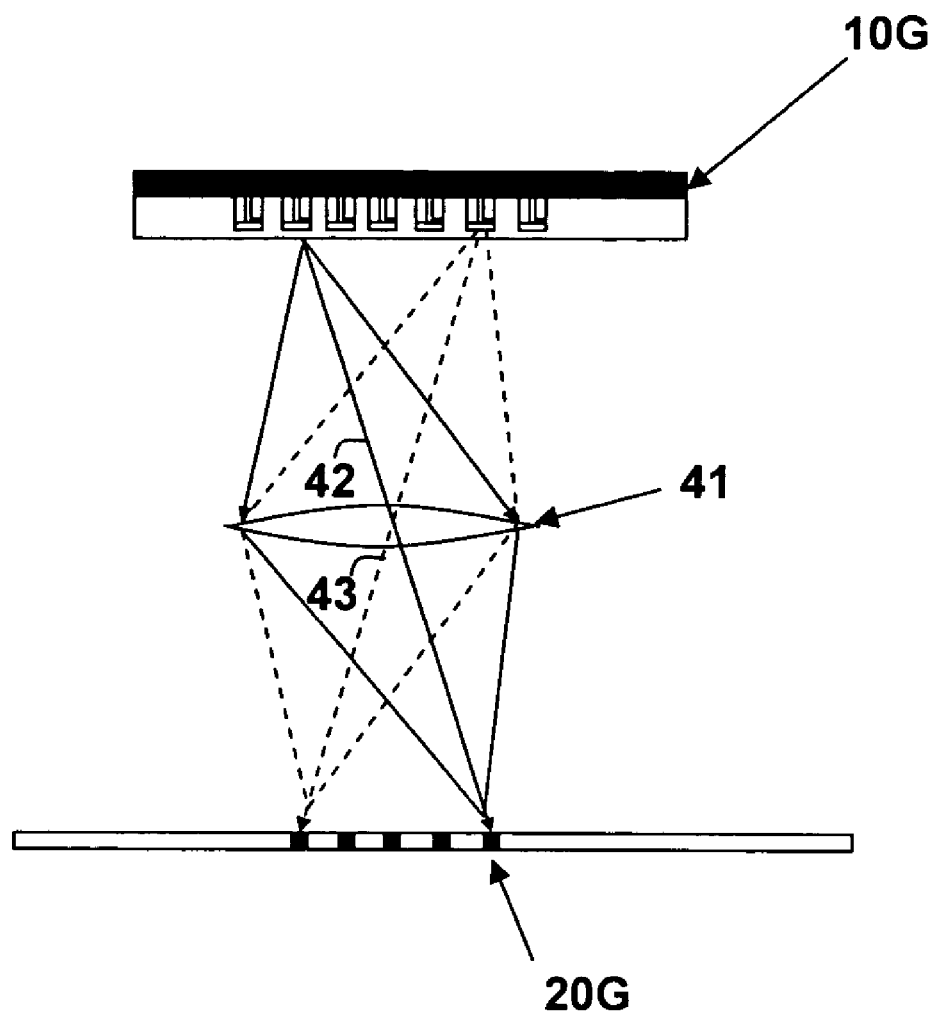
FIG. 4 is a pictorial diagram depicting details of an active sensor system in accordance another embodiment of the present invention.

Referring now to FIG. 4, an active sensor system in accordance with yet another embodiment of the present invention is depicted. Active sensor 10G, which may be any of the active sensors described above or variations thereon, is coupled by an imaging lens 41 to sample elements 20G. The imaging system may alternatively be or include optical fibers, waveguides of other type or any known method for "remoting" (or "relaying") an image from sample elements 20G to active sensor 10G. As long as a grouping via the image is made between illumination elements and detection elements within active sensor 10G, detection of individual sample element 20G behavior is provided. Optical paths (such as optical paths 42 and 43) associate co-located detection and illumination elements within active sensor 10G with a particular sample element (e.g., optical path 42 associates a particular detector/illuminator with sample element 20G). Alternatively, separate detection and illumination devices may be provided and coupled via beam-splitters, couplers or physical arrangement (angular orientation, etc.), so that an association between one or more detection elements and one or more illumination elements is preserved. While the embodiment shown uses a single lens 41 to relay light between active sensor 10G element groups and sample elements with an inverted position relationship, other lens/relaying-device configurations may be employed including position-rectified configurations.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An active sensor system for detecting optical behavior of one or more samples, said system comprising:
    at least one substrate;
    multiple illumination elements disposed on a first one of said at least one substrate, said illumination elements forming a multipixel illumination source, whereby portions of said samples are substantially uniquely illuminated by associated ones of said illumination elements;
    multiple detector elements disposed on a second one of said at least one substrate and forming a multipixel detector interspersed with said illumination elements, whereby light returning in response to said illumination from said portions of said samples are substantially uniquely detected by associated detector elements;
    an illumination control subsystem coupled to said multiple illumination elements for controlling said illumination of said portions of said samples; and
    a processing subsystem coupled to said multiple detector elements for producing an output indicating a detected optical signal corresponding to said light returning from said portions of said samples, and wherein said first one of said at least one substrate and said second one of said at least one substrate are the same substrate, and wherein said illumination elements are interspersed with said detection elements.

2. The active sensor system of claim 1, wherein said first one of said at least one substrate and said second one of said at least one substrate are separate substrates, and wherein said illumination elements are associated by position within the multipixel illumination source with detection elements having a corresponding position within the multipixel detector.

3. The active sensor system of claim 1, further comprising an imaging system for coupling an image from said multipixel illumination source to said samples, whereby said multipixel illumination source may be remotely located from said samples, while preserving the association of said illumination elements to said portions of said samples.

4. The active sensor system of claim 1, further comprising an imaging system for coupling an image from said multipixel detector to said samples, whereby said multipixel detector may be remotely located from said samples, while preserving the association of said detector elements to said portions of said samples.

5. The active sensor system of claim 1, wherein each of said multiple illumination elements is associated with a unique one of said detector elements.

6. The active sensor system of claim 1, wherein each of said multiple illumination elements is associated with a group of said detector elements having at least two members.

7. The active sensor system of claim 6, wherein each group of detector elements further comprises multiple filters having a unique optical characteristic, wherein each of said filters is coupled in the receiving path of an associated detector, whereby each group of detector elements resolves multiple optical characteristics of said returning light from an associated portion of said samples.

8. The active sensor system of claim 7, wherein said optical characteristic is a wavelength passband characteristic.

9. The active sensor system of claim 7, wherein said optical characteristic is a polarization characteristic.

10. The active sensor system of claim 1, wherein each of said multiple detector elements is associated with a group of said illumination elements having at least two members.

11. The active sensor system of claim 10, wherein each illumination element within each group of said illumination elements has a unique emission characteristic, whereby each group of illumination elements illuminates said associated portion of said samples with one or said unique characteristics in response to said illumination control subsystem.

12. The active sensor of claim 11, wherein each group of illumination elements further comprises multiple filters having a unique optical characteristic, each of said multiple filters within a given group coupled to the output of a unique illumination element within said given group, whereby each illumination element within each group of said illumination elements has a unique emission characteristic.

13. The active sensor system of claim 11, wherein said unique emission characteristic is a wavelength characteristic.

14. The active sensor system of claim 11, wherein said unique emission characteristic is a polarization characteristic.

15. The active sensor system of claim 1, further comprising multiple microlenses, each coupled to an output of an associated one or more of said illumination elements, whereby illumination from said associated illumination elements is focused on said associated portions of said samples.

16. The active sensor system of claim 1, further comprising multiple microlenses, each coupled to an output of an associated one or more of said detection elements, whereby fields of said associated detector elements are focused on said associated portions of said samples.

17. The active sensor system of claim 1, wherein said illumination control system and said processing subsystem are integrated on said one or more substrates.

18. The active sensor system of claim 1, wherein said multi-pixel illumination source and said multi-pixel detector each form a two-dimensional array of elements arranged in multiple rows and columns.

19. The active sensor system of claim 1, wherein said multi-pixel illumination source and said multi-pixel detector each form a one-dimensional array of elements arranged in a single row.

20. An active sensor for detecting optical behavior of one or more samples, said active sensor comprising a unified structure comprising:
    a substrate forming a bottom layer of said active sensor;
    multiple illumination elements disposed on said substrate, said illumination elements forming a multipixel illumination source, whereby portions of said samples are uniquely illuminated by associated ones of said illumination elements; and
    multiple detector elements disposed on said substrate and forming a multipixel detector interspersed with said illumination elements, whereby light returned from said portions of said samples in response to said illumination are detected by associated detector elements further associated with said illumination elements associated with said portion.

21. The active sensor of claim 20, further comprising:
    an illumination control subsystem integrated on said substrate and coupled to said multiple illumination elements for controlling said illumination of said portions of said samples; and
    a processing subsystem integrated on said substrate and coupled to said multiple detector elements for producing an output indicating detected fluorescence from said portions of said samples.

22. A method for measuring optical behavior of portions of one or more samples, said method comprising:
    illuminating portions of said one or more samples with a multipixel illuminator-detector having multiple illumination elements and multiple associated detection elements disposed on the same substrate, wherein each of said illumination elements and associated detection elements is associated with a unique one of said portions;
    detecting light returning from said portions of said one or more samples in response to said illuminating, said detecting performed by said illuminator-detector; and
    processing a result of said detecting to obtain a mapping of optical behavior of said one or more samples.

23. The method of claim 22, wherein said detecting detects emissions from each of said portions using a group of detectors each having a bandwidth-limited detection characteristic with respect to other members of said group, whereby said detection resolves multiple wavelengths of said returning light.

24. The method of claim 22, wherein said detecting detects emissions from each of said portions using a group of detectors each having a polarization-limited detection characteristic with respect to other members of said group, whereby said detection resolves multiple polarizations of said returning light.

25. The method of claim 22, further comprising focusing a field of each of said illumination elements on said associated portion.

26. The method of claim 22, further comprising focusing a field of each of said detection elements on said associated portion.

27. The method of claim 22, further comprising imaging a field of each of said illumination elements on said associated portion.

28. The method of claim 22, further comprising imaging a field of each of said detection elements on said associated portion.

29. The method of claim 22, wherein said illuminating comprises sequentially selecting one or more of said illumination elements, whereby selected ones of said associated portions are illuminated at one time.

30. The method of claim 22, wherein said illuminating comprises simultaneously illuminating all of said illumination elements.

31. The method of claim 22, further comprising remotely imaging said illuminating through an imaging system, whereby said illumination elements are remotely located from said portions of said samples.

32. The method of claim 22, further comprising remotely imaging said detecting through an imaging system, whereby said detection elements are remotely located from said portions of said samples.

33. The method of claim 22, further comprising placing said multipixel detector and said multipixel illuminator in close proximity to said one or more samples, whereby said portions of said samples are associated with unique detection elements and unique illumination elements by proximity.

* * * * *